US012729373B2

(12) United States Patent
Kim et al.

(10) Patent No.: US 12,729,373 B2
(45) Date of Patent: Sep. 8, 2026

(54) PORCINE STOMACH MUCOSAL TISSUE DECELLULARIZATION METHOD FOR CULTURING STOMACH OR STOMACH CANCER TISSUES, COMPOSITION FOR PRODUCING SCAFFOLD, AND METHOD FOR CULTURING TISSUE

(71) Applicant: POSTECH RESEARCH AND BUSINESS DEVELOPMENT FOUNDATION, Pohang-si (KR)

(72) Inventors: Ji Soo Kim, Daegu (KR); Jin Ah Jang, Pohang-si (KR); Dong Woo Cho, Seoul (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 557 days.

(21) Appl. No.: 18/274,532

(22) PCT Filed: Mar. 7, 2022

(86) PCT No.: PCT/KR2022/003139

§ 371 (c)(1),
(2) Date: Jul. 27, 2023

(87) PCT Pub. No.: WO2022/191533

PCT Pub. Date: Sep. 15, 2022

(65) Prior Publication Data

US 2024/0084263 A1 Mar. 14, 2024

(30) Foreign Application Priority Data

Mar. 8, 2021 (KR) ........................ 10-2021-0029911

(51) Int. Cl.

| | |
|---|---|
| ***C12N 5/071*** | (2010.01) |
| ***A61K 35/38*** | (2015.01) |
| ***A61L 27/38*** | (2006.01) |
| ***B33Y 70/00*** | (2020.01) |
| ***C12N 5/00*** | (2006.01) |

(52) U.S. Cl.

CPC ............ *C12N 5/0679* (2013.01); *A61K 35/38* (2013.01); *A61L 27/3804* (2013.01); *B33Y 70/00* (2014.12); *C12N 5/0068* (2013.01); *C12N 2509/00* (2013.01)

(58) Field of Classification Search

None

See application file for complete search history.

(56) References Cited

U.S. PATENT DOCUMENTS

2018/0126037 A1 5/2018 Huh et al.

FOREIGN PATENT DOCUMENTS

| | | |
|---|---|---|
| KR | 10-2017-0078460 | 7/2017 |
| KR | 10-2017-0079449 | 7/2017 |
| KR | 10-2019-0077290 | 7/2019 |
| KR | 10-2019-0125213 | 11/2019 |
| WO | 2010-014021 | 2/2010 |

OTHER PUBLICATIONS

Gilpin et al, Decellularization Strategies for Regenerative Medicine: From Processing Techniques to Applications, BioMed Research International vol. 2017 (Year: 2017).*

Giobbe et al, Extracellular matrix hydrogel derived from decellularized tissues enables endodermal organoid culture, Nature Communications (Year: 2019).*

Mendibil et al, Tissue-Specific Decellularization Methods: Rationale and Strategies to Achieve Regenerative Compounds, International Journal of Molecular Sciences (Year: 2020).*

* cited by examiner

*Primary Examiner* — Allison M Fox
*Assistant Examiner* — Marisol Ann O'Neill
(74) *Attorney, Agent, or Firm* — LEX IP MEISTER, PLLC

(57) ABSTRACT

The present invention relates to a method for decellularization of porcine stomach mucosal tissue for culturing stomach tissue or stomach cancer tissue, a composition for producing a scaffold, and a method for culturing tissue, and particularly, to: a method for decellularization of porcine stomach mucosal tissue comprising chopping porcine stomach mucosal tissue and performing first treatment, second treatment, washing, and third treatment; a decellularization product composed of porcine stomach mucosal tissue decellularized by the method; a composition for producing a stomach tissue or stomach cancer tissue culture scaffold containing a pepsin digest of the decellularization product; and a method for culturing stomach tissue or stomach cancer tissue comprising adding stomach cells or stomach cancer cells to the composition, followed by shaping to produce a tissue culture scaffold containing stomach cells or stomach cancer cells, and incubating the scaffold in a medium.

12 Claims, 5 Drawing Sheets

[FIG. 1]
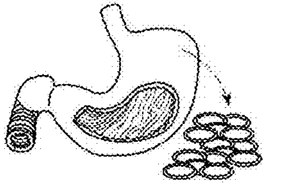
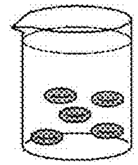
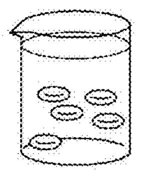
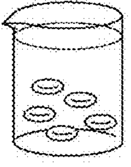
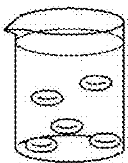
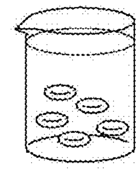
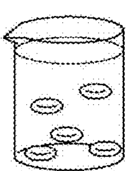
[FIG. 2]
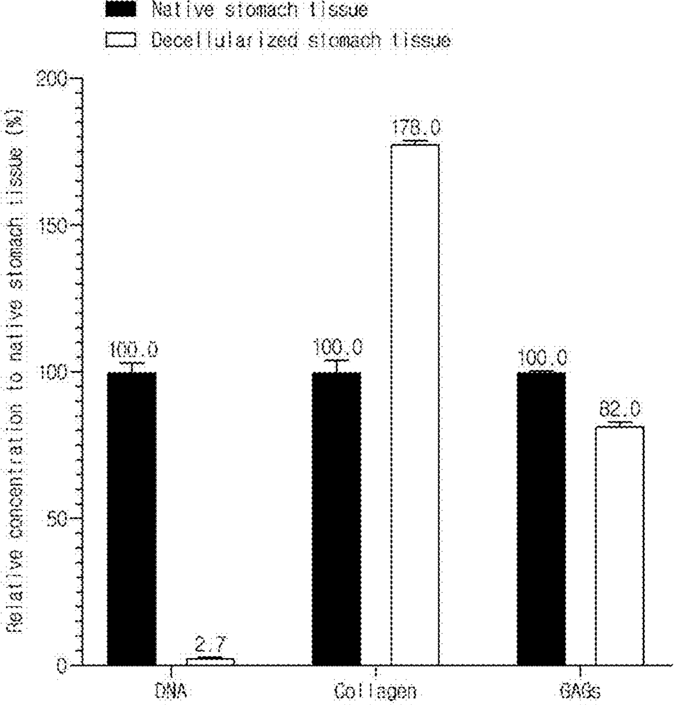

[FIG. 3]
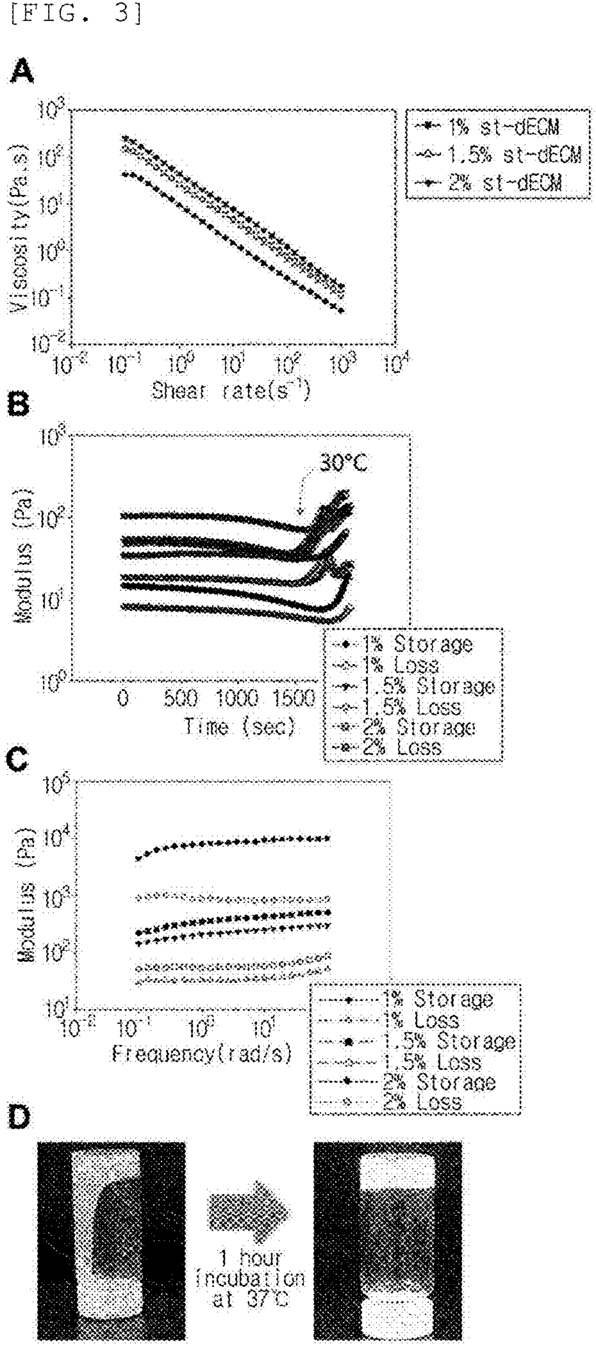

[FIG. 4]
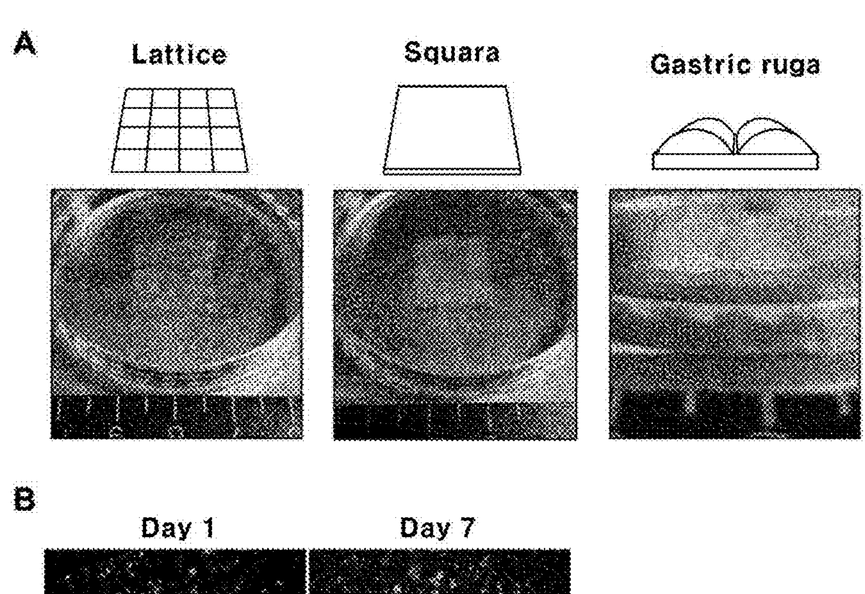
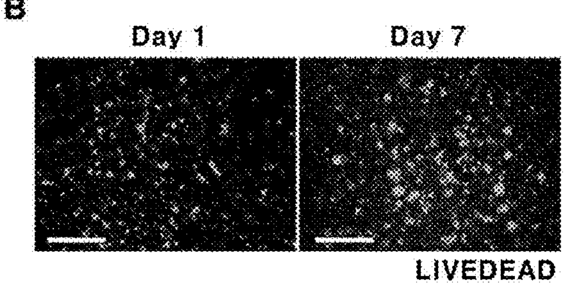
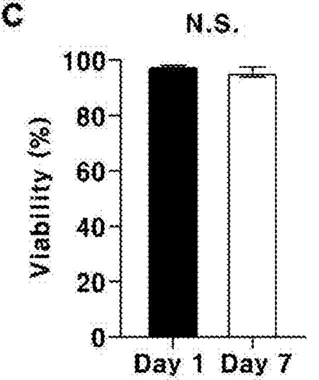

[FIG. 5]
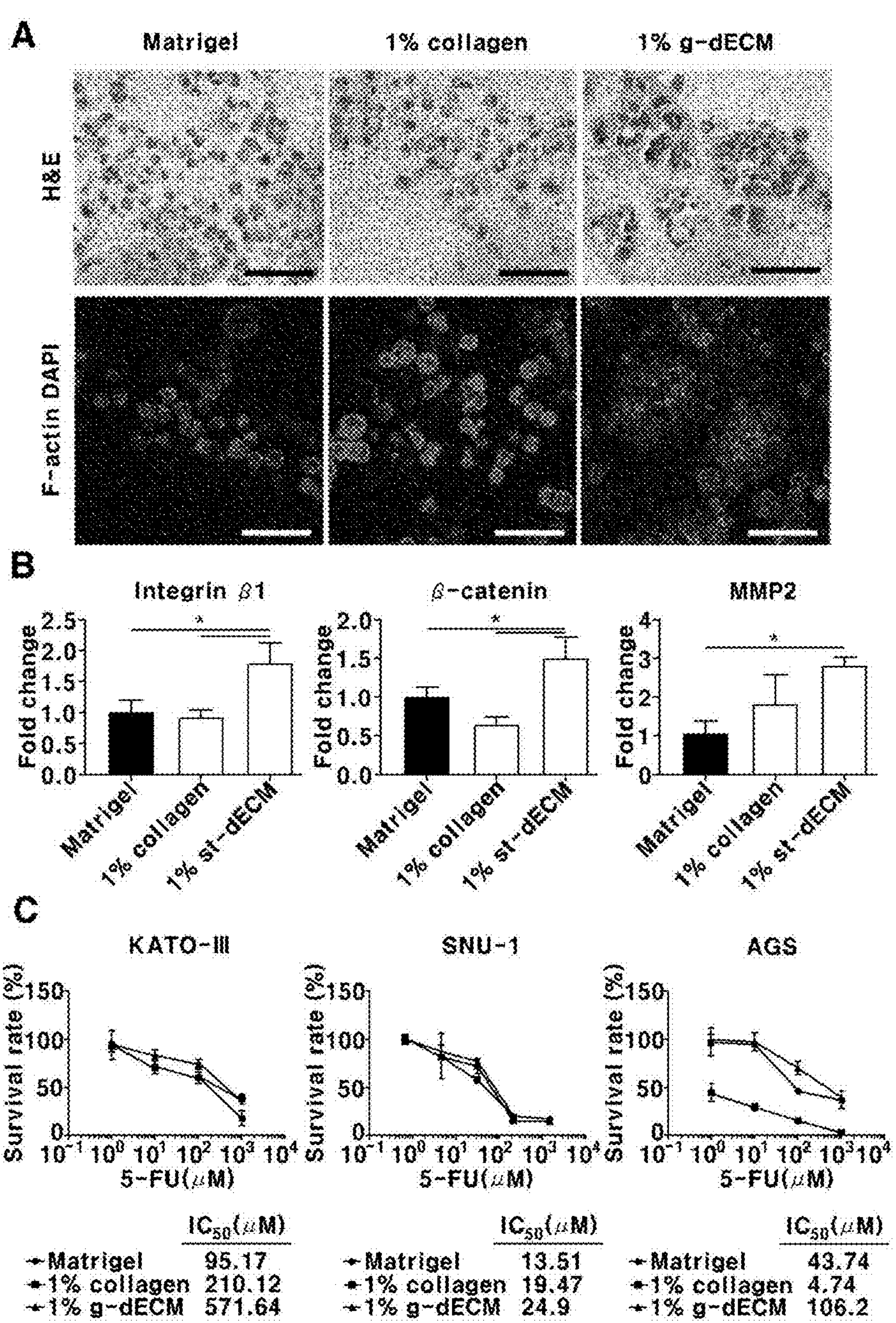

[FIG. 6]
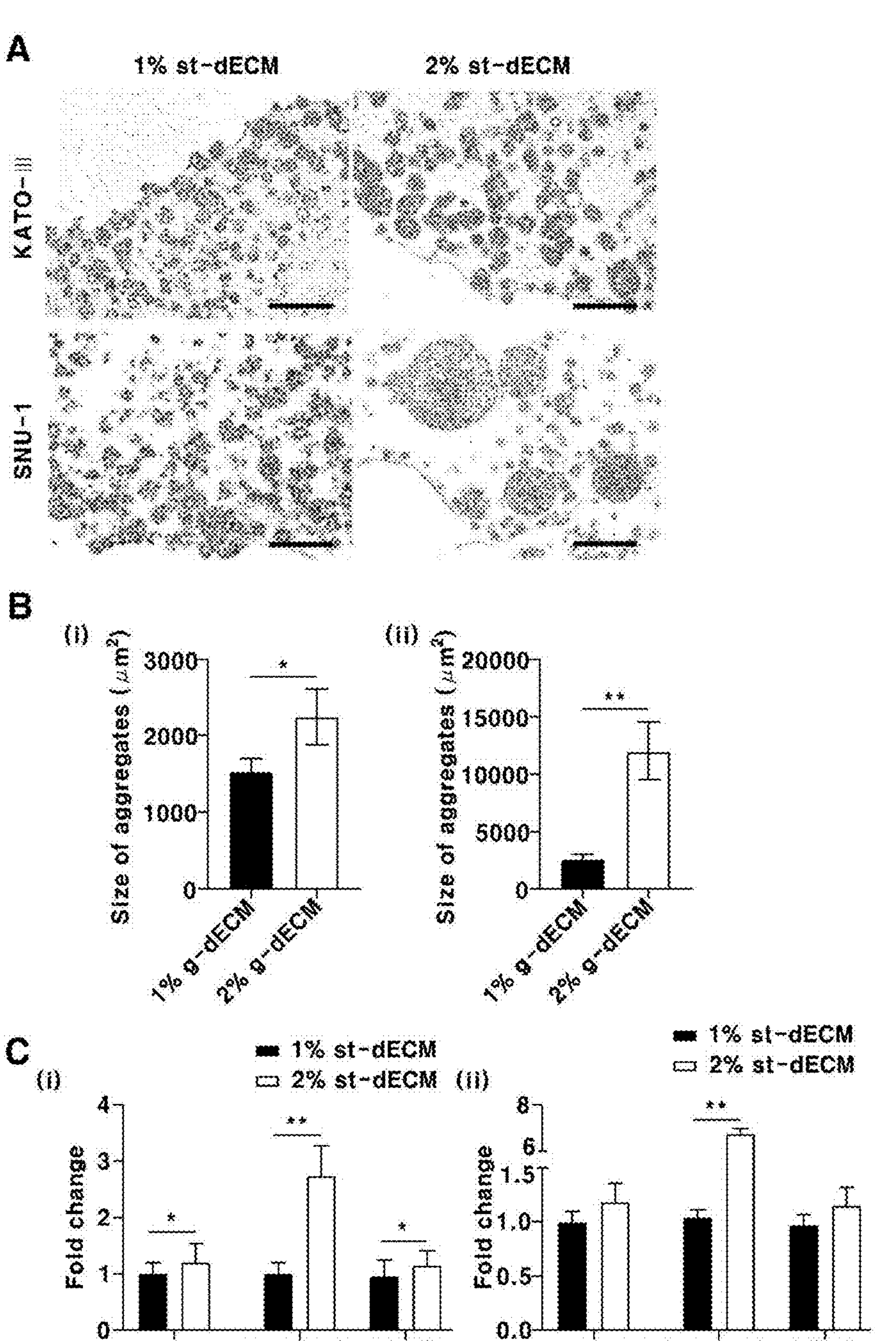

PORCINE STOMACH MUCOSAL TISSUE DECELLULARIZATION METHOD FOR CULTURING STOMACH OR STOMACH CANCER TISSUES, COMPOSITION FOR PRODUCING SCAFFOLD, AND METHOD FOR CULTURING TISSUE

TECHNICAL FIELD

The present invention relates to a method for decellularization of porcine stomach mucosal tissue for culturing stomach tissue or stomach cancer tissue, a composition for producing a scaffold, and a method for culturing tissue, and particularly, to a method for decellularization of porcine stomach mucosal tissue comprising chopping porcine stomach mucosal tissue and performing first treatment, second treatment, washing, and third treatment, a decellularization product composed of porcine stomach mucosal tissue decellularized by the method, a composition for producing a stomach tissue or stomach cancer tissue scaffold comprising a pepsin digest of the decellularization product, and a method for culturing stomach tissue or stomach cancer tissue comprising adding stomach cells or stomach cancer cells to the composition, followed by shaping to produce a tissue culture scaffold containing stomach cells or stomach cancer cells, and culturing the scaffold in a medium.

BACKGROUND ART

Stomach cancer has a high incidence and mortality rate worldwide, but to date, only surgery has been performed as the only method for completely removing local tumors. However, because end-stage stomach cancer patients are difficult to treat with surgery alone, chemotherapy is essentially performed in combination with surgery, but the patients show high drug resistance and show low survival rates due to the absence of effective therapeutic drugs.

In order to find drugs for treating stomach cancer patients, in vitro culture methods for stomach tissue or stomach cancer tissue have been developed. However, these methods have a disadvantage in that they cannot reproduce characteristics such as the specific structure, mechanical properties, and biochemical components of primary stomach cancer tissue, as well as action between various cells constituting the tumor tissue. Accordingly, it is necessary to develop an in vitro stomach tissue or stomach cancer tissue culture technology capable of reproducing the characteristics of primary stomach cancer tissue by providing stomach cells or stomach cancer cells with an environment similar to the stomach.

Techniques using bioscaffolds produced by decellularizing animal tissues for tissue culture are known. However, a conventional stomach tissue culture technique is a technique of simply culturing cells in two dimensions by decellularizing the whole stomach tissue, and has problems in that sufficient decellularization is not achieved, extracellular matrix components such as glycosaminoglycans (GAGs) are greatly lost during the decellularization process, and an enzyme called DNase is used.

Accordingly, the present inventors have attempted to develop a technology that enables safer and more efficient stomach tissue or stomach cancer tissue culture while providing stomach cells or stomach cancer cells with an environment more similar to the stomach.

PRIOR ART DOCUMENTS

[Non-Patent Document]

Zambaiti, Elisa, et al. "Whole rat stomach decellularisation using a detergent-enzymatic protocol." Pediatric surgery international 35.1 (2019): 21-27.

DISCLOSURE

Technical Problem

Therefore, a main object of the present invention is to provide a method that enables safer and more efficient stomach tissue or stomach cancer tissue culture while providing stomach cells or stomach cancer cells with an environment more similar to the stomach.

In this regard, another object of the present invention is to provide a method for decellularization of porcine stomach mucosal tissue, which is a technique related to the production of a scaffold for providing stomach cells or stomach cancer cells with an environment similar to the stomach, is capable of sufficient decellularization without using enzymes such as DNase, and is capable of reducing loss of extracellular matrix components.

Still another object of the present invention is to provide a composition for efficiently producing a stomach tissue or stomach cancer tissue culture scaffold using a decellularization product obtained by decellularization.

Technical Solution

According to one aspect of the present invention, the present invention provides a method for decellularization of porcine stomach mucosal tissue comprising: a chopping step of chopping porcine stomach mucosal tissue; a first treatment step of brining the chopped porcine stomach mucosal tissue into contact with a solution containing sodium dodecyl sulfate and ethylenediaminetetraacetic acid; a second treatment step of bringing the stomach mucosal tissue, subjected to the first treatment step, into contact with a solution containing Triton X-100 and ethylenediaminetetraacetic acid; a washing step of washing the stomach mucosal tissue subjected to the second treatment step; and a third treatment step of bringing the stomach mucosal tissue, subjected to the washing step, into contact with a solution containing peracetic acid and ethanol.

In the method for decellularization of porcine stomach mucosal tissue according to the present invention, the chopping step is preferably a step of chopping the porcine stomach mucosal tissue to a thickness of 1 to 3 mm.

In the method for decellularization of porcine stomach mucosal tissue according to the present invention, the solution in the first treatment step is preferably a solution containing 0.5 to 2% (w/v) sodium dodecyl sulfate and 10 to 100 mM ethylenediaminetetraacetic acid.

In the method for decellularization of porcine stomach mucosal tissue according to the present invention, the solution in the second treatment step is preferably a solution containing 0.5 to 2% (w/V) Triton X-100 (polyethylene glycol p-(1,1,3,3-tetramethylbutyl)-phenyl ether) and 10 to 100 mM ethylenediaminetetraacetic acid.

In the method for decellularization of porcine stomach mucosal tissue according to the present invention, the solution in the third treatment step is preferably a solution containing 0.05 to 0.2% (w/v) peracetic acid and 2 to 8% (v/v) ethanol.

In the method for decellularization of porcine stomach mucosal tissue according to the present invention, the first treatment step is preferably a step of immersing and maintaining the chopped porcine stomach mucosal tissue in the solution containing sodium dodecyl sulfate and ethylenediaminetetraacetic acid for 12 to 48 hours.

In the method for decellularization of porcine stomach mucosal tissue according to the present invention, the second treatment step is preferably a step of immersing and maintaining the stomach mucosal tissue, subjected to the first treatment step, in the solution containing Triton X-100 and ethylenediaminetetraacetic acid for 12 to 48 hours.

In the method for decellularization of porcine stomach mucosal tissue according to the present invention, the third treatment step is preferably a step of immersing and maintaining the stomach mucosal tissue, subjected to the washing step, in the solution containing peracetic acid and ethanol for 1 to 4 hours.

In the method for decellularization of porcine stomach mucosal tissue according to the present invention, the washing step is preferably a step of washing the stomach mucosal tissue, subjected to the second treatment step, with phosphate buffered saline.

According to another aspect of the present invention, the present invention provides a decellularization product composed of a porcine stomach mucosal tissue decellularized by the above method.

According to still another aspect of the present invention, the present invention provides a composition for producing a stomach tissue or stomach cancer tissue culture scaffold containing a pepsin digest of the decellularization product.

In the composition for producing a stomach tissue or stomach cancer tissue culture scaffold according to the present invention, the composition is preferably prepared by adding the decellularization product to an acetic acid-containing solution and adding pepsin thereto.

In the composition for producing a stomach tissue or stomach cancer tissue culture scaffold according to the present invention, the composition is preferably prepared by adding, to a 0.25 to 1M acetic acid solution, the decellularization product at 0.5 to 4% (w/w) and pepsin at 0.025 to 0.8% (w/w).

According to yet another aspect of the present invention, the present invention provides a method for culturing stomach tissue or stomach cancer tissue comprising: a step of producing a tissue culture scaffold containing stomach cells or stomach cancer cells by adding stomach cells or stomach cancer cells to the above composition, followed by shaping; and a culture step of culturing the tissue culture scaffold containing stomach cells or stomach cancer cells in a medium.

In the method for culturing stomach tissue or stomach cancer tissue according to the present invention, the shaping is preferably performed by 3D printing.

In the method for culturing stomach tissue or stomach cancer tissue according to the present invention, the method preferably further comprises, before the culture step, a thermal crosslinking step of heat-treating the tissue culture scaffold containing stomach cells or stomach cancer cells at 35 to 40° C.

Advantageous Effects

According to the tissue culture method of the present invention, it is possible to culture stomach tissue or stomach cancer tissue safely and efficiently using porcine stomach mucosal tissue. According to the decellularization method of the present invention, it is possible to decellularize porcine stomach mucosal tissue efficiently without using enzymes such as DNase while reducing loss of extracellular matrix components. In addition, when the composition of the present invention is used, it is possible to efficiently produce a tissue culture scaffold capable of providing stomach cells or stomach cancer cells with an environment similar to the stomach.

BRIEF DESCRIPTION OF DRAWINGS

FIG. 1 shows a method for decellularization of porcine stomach mucosal tissue according to an example of the present invention.

FIG. 2 shows the results of analyzing the concentrations of DNA, collagen and glycosaminoglycan (GAG) in a decellularization product (st-dECM) according to an example of the present invention by a biochemical analysis method.

FIG. 3 shows the results of analyzing the viscosity and modulus (A to C) and sol-gel behavior of a composition (st-dECM bioink) for producing a tissue culture scaffold according to an example of the present invention.

FIG. 4 shows the result of encapsulating and printing stomach cancer cells in a composition for producing a tissue culture scaffold (st-dECM bioink) according to an example of the present invention (A), and the result of analyzing the cell viability of the printed stomach cancer cell-containing tissue culture scaffold during long-term culture (B and C).

FIG. 5 shows the results of analyzing the stomach cancer cell morphology by histological staining (A), the expression levels of malignancy markers in stomach cancer cells (B), and the drug resistance of stomach cancer cells (C), after culturing a stomach cancer cell-containing tissue culture scaffold obtained by encapsulating and printing stomach cancer cells in a composition (st-dECM bioink) for producing a tissue culture scaffold according to an example of the present invention, stomach cancer cell-containing Matrigel, and stomach cancer cell-containing collagen.

FIG. 6 shows the results of analyzing stomach cancer cell aggregation (A and B) and expression levels of malignancy markers (C), after encapsulating and culturing stomach cancer cells (KATO3 or SNU-1) in tissue culture scaffold-producing compositions (st-dECM bioink) prepared to have different concentrations of a decellularization product (st-dECM) according to an example of the present invention.

BEST MODE

A method for decellularization of porcine stomach mucosal tissue according to the present invention comprises: a chopping step of chopping porcine stomach mucosal tissue; a first treatment step of brining the chopped porcine stomach mucosal tissue into contact with a solution containing sodium dodecyl sulfate and ethylenediaminetetraacetic acid; a second treatment step of bringing the stomach mucosal tissue, subjected to the first treatment step, into contact with a solution containing Triton X-100 and ethylenediaminetetraacetic acid; a washing step of washing the stomach mucosal tissue subjected to the second treatment step; and a third treatment step of bringing the stomach mucosal tissue, subjected to the washing step, into contact with a solution containing peracetic acid and ethanol.

The decellularization method according to the present invention is a method capable of decellularization sufficient to provide particularly a stomach tissue or stomach cancer tissue culture scaffold material without using an enzyme such as DNase, and is capable of preventing problems caused by using DNase, such as destruction of connective tissue fibers.

In addition, the decellularization method according to the present invention enables more efficient tissue culture by reducing the loss of extracellular matrix components such as glycosaminoglycan (GAG), which occurs during the decellularization process.

In the decellularization method according to the present invention, the porcine stomach mucosal tissue to be decellularized is preferably a mucosa tissue. The mucosa layer is one of the four layers of the stomach: mucosa, submucosa, muscularis externa, and serosa. Although it is preferable to use only the mucosa layer as described above, decellularization may be achieved even if the other layers are partially included.

In the decellularization method according to the present invention, the chopping step may be performed using a conventional device or apparatus that is used for chopping animal tissues. Preferably, the stomach mucosal tissue is chopped to a thickness of 0.5 to 5 mm, more preferably 1 to 3 mm. This chopping step enables more efficient decellularization by widening the contact area between the stomach mucosal tissue and the solution in a subsequent step.

In the decellularization method according to the present invention, the first treatment step is a step of bringing the chopped porcine stomach mucosal tissue into contact with a solution containing sodium dodecyl sulfate (SDS) and ethylenediaminetetraacetic acid (EDTA), that is, a first treatment solution, and may be performed using a conventional method that is used for contact between biological tissue or cells and the solution for reaction between them. Preferably, a method of immersing the tissue in the first treatment solution is used. More preferably, a method of immersing and stirring the tissue in the first treatment solution is used. At this time, the stirring is preferably performed at a rotational speed of 10 to 200 rpm, more preferably 20 to 150 rpm, more preferably 30 to 100 rpm. At this time, the volume of the first treatment solution is preferably at least 2 times, more preferably at least 5 times, still more preferably at least 10 times the volume of the tissue. The contact time between the tissue and the first treatment solution is preferably 1 to 100 hours, more preferably 5 to 50 hours, still more preferably 12 to 48 hours, still more preferably 20 to 30 hours. The temperature during contact is preferably 0 to 20° C., more preferably 2 to 16° C., still more preferably 4 to 16° C. The first treatment solution is preferably a solution containing 0.5 to 2% (w/v) sodium dodecyl sulfate and 10 to 100 mM ethylenediaminetetraacetic acid, more preferably a solution containing 0.7 to 1.5% (w/v) sodium dodecyl sulfate and 10 to 50 mM ethylenediaminetetraacetic acid, still more preferably a solution containing 0.8 to 1.2% (w/v) sodium dodecyl sulfate and 20 to 30 mM ethylenediaminetetraacetic acid.

In the decellularization method according to the present invention, the second treatment step is a step of bringing the stomach mucosal tissue, subjected to the first treatment step, into contact with a solution containing sodium dodecyl sulfate (SDS) and ethylenediaminetetraacetic acid (EDTA), that is, a second treatment solution, and this step may also be performed using a conventional method that is used for contact between biological tissue or cells and the solution for reaction between them. Preferably, a method of immersing the tissue in the second treatment solution is used. More preferably, a method of immersing and stirring the tissue in the second treatment solution is used. At this time, the stirring is preferably performed at a rotational speed of 10 to 200 rpm, more preferably 20 to 150 rpm, more preferably 30 to 100 rpm. At this time, the volume of the second treatment solution is preferably at least 2 times, more preferably at least 5 times, still more preferably at least 10 times the volume of the tissue. The contact time between the tissue and the second treatment solution is preferably 1 to 100 hours, more preferably 5 to 50 hours, still more preferably 12 to 48 hours, still more preferably 20 to 30 hours. The temperature during contact is preferably 0 to 20° C., more preferably 2 to 16° C., still more preferably 4 to 16° C. The second treatment solution is preferably a solution containing 0.5 to 2% (w/v) Triton X-100 and 10 to 100 mM ethylenediaminetetraacetic acid, more preferably a solution containing 0.7 to 1.5% (w/v) Triton X-100 and 10 to 50 mM ethylenediaminetetraacetic acid, still more preferably a solution containing 0.8 to 1.2% (w/v) Triton X-100 and 20 to 30 mM ethylenediaminetetraacetic acid.

In the decellularization method according to the present invention, the washing step is a step of removing the compounds used in the first treatment and the second treatment and present in the stomach mucosal tissue, and may be performed using a conventional method that is used wash out compounds after treating biological tissue or cells with the compounds. Preferably, the compounds are washed out with phosphate buffered saline (PBS). Preferably, a method of immersing the tissue in a washing solution, for example, phosphate buffered saline, is used. More preferably, a method of immersing and stirring the tissue in the washing solution is used. At this time, the stirring is preferably performed at a rotational speed of 10 to 200 rpm, more preferably 20 to 150 rpm, more preferably 30 to 100 rpm. At this time, the volume of the washing solution is preferably at least 2 times, more preferably at least 5 times, still more preferably at least 10 times the volume of the tissue. The washing time, for example, the immersion time of the tissue in the washing solution, is preferably 1 to 100 hours, more preferably 5 to 50 hours, still more preferably 12 to 48 hours, still more preferably 20 to 30 hours. The temperature during washing is preferably 0 to 20° C., more preferably 2 to 16° C., still more preferably 4 to 16° C.

In the decellularization method according to the present invention, the third treatment step is a step of bringing the stomach mucosal tissue, subjected to the washing step, into contact with a solution containing peracetic acid and ethanol, that is, a third treatment solution, and this step may also be performed using a conventional method that is used for contact between biological tissue or cells and the solution for reaction between them. Preferably, a method of immersing the tissue in the third treatment solution is used. More preferably, a method of immersing and stirring the tissue in the third treatment solution is used. At this time, the stirring is preferably performed at a rotational speed of 10 to 200 rpm, more preferably 20 to 150 rpm, more preferably 30 to 100 rpm. At this time, the volume of the third treatment solution is preferably at least 2 times, more preferably at least 5 times, still more preferably at least 10 times the volume of the tissue. The contact time between the tissue and the third treatment solution is preferably 10 minutes to 8 hours, more preferably 30 minutes to 6 hours, still more preferably 1 hour to 4 hours, still more preferably 1 hour to 3 hours. The temperature during contact is preferably 0 to 20° C., more preferably 2 to 16° C., still more preferably 4 to 16° C. The third treatment solution is preferably a solution containing 0.05 to 0.2% (w/v) peracetic acid and 2 to 8% (v/v) ethanol, more preferably a solution containing 0.07 to 0.15% (w/v) peracetic acid and 2 to 6% (v/v) ethanol, still more preferably a solution containing 0.08 to 0.12% (w/v) peracetic acid and 3 to 5% (v/v) ethanol.

The decellularization method according to the present invention preferably further comprises, before the first treatment step, a pre-first-treatment washing step of washing the chopped porcine stomach mucosal tissue. At this time, the tissue is preferably washed with water. For specific details, refer to the washing step, but the washing time is preferably 1 minute to 2 hours, more preferably 5 minutes to 1 hour, still more preferably 10 minutes to 50 minutes, still more preferably 20 minutes to 40 minutes.

The decellularization method according to the present invention preferably further comprises a freeze-drying step of freeze-drying the stomach mucosal tissue subjected to the third treatment step. At this time, freeze-drying may be performed using a conventional method and device or apparatus that is used to freeze-dry materials of biological origin.

The decellularization method according to the present invention preferably further comprises, before the freeze-drying step, a pre-freeze-drying washing step of washing the stomach mucosal tissue subjected to the third treatment step. At this time, the tissue is preferably washed with phosphate buffered saline or water. More preferably, the tissue is washed with phosphate buffered saline and then with water.

The decellularization product according to the present invention is a tissue decellularized by the decellularization method, and may have a DNA concentration of 5% or less, more preferably at least 3% and a glycosaminoglycan concentration of 70% or more, more preferably 80% or more, relative to those in the stomach mucosal tissue before decellularization.

The composition for producing a stomach tissue or stomach cancer tissue culture scaffold according to the present invention is characterized by comprising a pepsin digest of the decellularization product described above.

The composition for producing a stomach tissue or stomach cancer tissue culture scaffold according to the present invention is preferably bio-ink, more preferably bio-ink for 3D printing.

The composition for producing a stomach tissue or stomach cancer tissue culture scaffold according to the present invention is preferably prepared by adding the decellularization product to an acetic acid-containing solution and adding pepsin thereto. At this time, the acetic acid-containing solution is preferably a 0.25 to 1M acetic acid solution, more preferably a 0.3 to 0.8M acetic acid solution, more preferably a 0.4 to 0.6M acetic acid solution. Preferably, to the acetic acid-containing solution, the decellularization product is added at 0.5 to 4% (w/w) and pepsin is added at 0.025 to 0.8% (w/w). More preferably, to the acetic acid-containing solution, the decellularization product is added at 0.5 to 3% (w/w) and pepsin is added at 0.05 to 0.4% (w/w). Still more preferably, to the acetic acid-containing solution, the decellularization product is added at 1 to 2% (w/w) and pepsin is added at 0.1 to 0.2% (w/w). The resulting composition may have properties particularly useful for 3D printing.

The method for culturing stomach tissue or stomach cancer tissue according to the present invention comprises: a step of producing a tissue culture scaffold containing stomach cells or stomach cancer cells by adding stomach cells or stomach cancer cells to the composition for producing a stomach tissue or stomach cancer tissue scaffold, followed by shaping; and a culture step of culturing the tissue culture scaffold containing stomach cells or stomach cancer cells in a medium.

In the method for culturing stomach tissue or stomach cancer according to the present invention, the shaping may be performed using a conventional shaping method in which a flowable composition containing mutually aggregable materials is used as a shaping raw material and shaped into a specific shape. Preferably, the composition is shaped by 3D printing.

The method for culturing stomach tissue or stomach cancer according to the present invention preferably further comprises, before the culture step, a thermal crosslinking step of heat-treating the tissue culture scaffold containing stomach cells or stomach cancer cells at 35 to 40° C. At this time, the heat treatment temperature is preferably 36 to 39° C., more preferably 36 to 38° C. Through this step, the tissue culture scaffold may have characteristics particularly suitable for stomach cancer tissue culture.

In the method for culturing stomach tissue or stomach cancer according to the present invention, the stomach cells or stomach cancer cells may be added to the composition at a concentration of, for example, $10^5$ to $10^7$ cells/ml.

In the present invention, the stomach cells or stomach cancer cells may be stomach cells or stomach cancer cells derived from mammals, for example, non-human primates such as chimpanzees, humans, cows, sheep, pigs, goats, horses, dogs, cats, mice, and guinea pigs. More preferably, they are stomach cells or stomach cancer cells isolated from human stomach tissue or stomach cancer tissue.

Hereinafter, the present invention will be described in more detail with reference to examples. These examples are intended merely to illustrate the present invention, and the scope of the present invention is not to be construed as being limited by these examples.

Examples

1. Stomach Mucosal Tissue Decellularization and Hydrogel Production

Decellularization of stomach mucosal tissue was performed through the following process (FIG. 1).

1) Stomach mucosal tissue preparation: Stomach mucosal tissue (mucosa) was collected from the porcine stomach and chopped into small pieces having a thickness of 1 to 3 mm.

2) The chopped stomach mucosal tissue was washed by immersion in water for 30 minutes.

3) The washed stomach mucosal tissue was subjected to first treatment by immersion in a solution containing 1% (w/v) sodium dodecyl sulfate (SDS) and 25 mM ethylenediaminetetraacetic acid (EDTA) for 24 hours.

4) The stomach mucosal tissue subjected to first treatment was subjected to second treatment by immersion in a solution containing 1% (w/v) Triton X-100 and 25 mM EDTA for 24 hours.

5) The stomach mucosal tissue subjected to second treatment was washed by immersion in phosphate buffered saline (PBS) for 24 hours.

6) The stomach mucosal tissue washed with PBS was subjected to third treatment by immersion in a solution containing 0.1% (w/v) peracetic acid and 4% (v/v) ethanol for 2 hours.

7) The stomach mucosal tissue subjected to third treatment was washed three times with PBS and washed once with water.

8) The washed stomach mucosal tissue was freeze-dried.

All of the above steps were performed at a temperature of 16° C. or lower, and washing and first to third treatments were performed while stirring at a rotational speed of 30 to 200 rpm using an agitator. In addition, the volume of the solution used in each of washing and first to third treatments was at least 10 times the volume of the stomach mucosal tissue.

Decellularized extracellular matrix (st-dECM) (decellularization product of the present invention) was obtained by decellularizing stomach mucosal tissue through the above-described method.

As a result of quantifying DNA, collagen, and glycosaminoglycans (GAG) contained in st-dECM by a biochemical analysis method, it was confirmed that the amount of DNA remaining after decellularization was 2.7% of that in the tissue before decellularization, indicating that the cells were sufficiently removed through the decellularization process, and the remaining amounts of GAG and collagen were 82% and 178%, respectively (FIG. 2).

GAG is an aggregate of stomach extracellular matrix molecules that is related not only to the growth of stomach cells but also to angiogenesis and cancer metastasis in stomach cancer. Therefore, these results indicate that the decellularization method of the present invention ensures the maintenance of extracellular matrix components important for stomach cell or stomach cancer cell behavior.

2. Bioink Preparation and 3D Printing Using Decellularized Extracellular Matrix

Bioink (the composition for producing a tissue culture scaffold according to the present invention) was prepared through the pepsin digestion-mediated extracellular matrix liquefaction of the st-dECM.

In this Example, st-dECM was liquefied by treatment with a 0.5M acetic acid solution and 10 wt %, based on st-dECM, of pepsin. Specifically, bioink was prepared by adding, to a 0.5M acetic acid solution, st-dECM at 1% (w/w) and pepsin at 0.1% (w/w).

In order to confirm compatibility with an extrusion-based 3D cell printing system and whether the prepared bioink exhibits thermal crosslinking and shear peeling behaviors, which are essential properties for providing mechanical properties to tissue analogs, the rheological properties of the prepared bioink were investigated.

When the viscosity of the bioink was measured while increasing shear rate gradually at 4° C., the viscosity of the bioink tended to decrease (FIG. 3A). This means that the bioink of the present invention exhibits shear peeling behavior, which is essential for passage through small-diameter nozzles.

Next, the present inventors evaluated the gelation kinetics of the bioink by measuring complex metric components while increasing the temperature from 4° C. to 37° C. The complex modulus of the bioink increased rapidly for 10 minutes after reaching 37° C., and then the rate of the increase slowed down (FIG. 3B). In addition, it was shown that, when the liquid bioink was incubated at 37° C. for 30 minutes, the storage modulus thereof was higher than the loss modulus (FIG. 3C). This supports that the bioink of the present invention, which was in a liquid phase, exhibits thermal crosslinking behavior at 37° C.

In order to confirm the printability of the bioink, the bioink encapsulated with stomach cancer cells was 3D printed according to a predetermined pattern (FIG. 3D), and incubated for 7 days after 3D printing and thermal crosslinking. As a result of staining the structure with calcein AM, which labels viable stomach cancer cells, it was confirmed that the cells remained in a viable state. This shows that the bioink of the present invention may be used to print stomach cancer cells and to prepare various stomach cancer tissue models.

A method of culturing stomach cancer tissue using the bioink was as follows.

1) Stomach cancer cells were encapsulated in 1% st-dECM bioink at a concentration of $5\times10^6$ cells/ml.

2) The cells were printed according to a designed pattern (FIG. 4A).

3) Thermal crosslinking was induced in an incubator at 37° C. for about 1 hour.

4) The stomach cancer cells were cultured using RPMI 1640 (supplemented with 10% FBS and 1% penicillin/streptomycin) medium.

The above-described method enabled long-term culture of stomach cancer tissue (FIGS. 4B and C).

As a result of comparing the morphology of cultured stomach cancer cells with Matrigel and collagen experimental groups through histological staining, it could be confirmed that the stomach cancer cells cultured by the culture method of the present invention using the st-dECM bioink grew together in clusters as in actual cancer patients. On the other hand, stomach cancer cells in Matrigel and collagen did not grow in clusters (FIG. 5A).

In addition, the expression levels of malignancy markers of cancer were examined through β-catenin (cell-cell interaction marker), MMP2 (tissue remodeling marker), and integrin β1 (cell-ECM interaction marker), and it was confirmed that the expression levels were higher in the culture method of the present invention using st-dECM bioink (FIG. 5B). In addition, the stomach cancer tissue cultured in each hydrogel was treated with 5-FU, which is a drug commonly used in stomach cancer, and the culture method of the present invention using st-dECM bioink showed the highest drug resistance (FIG. 5C). This suggests that the tissue cultured by the culture method of the present invention may be used to predict the response of tumor tissue in vivo because it has higher drug resistance than the tissue cultured in Matrigel or collagen. As such, the results in the culture method of the present invention, which show higher expression levels of malignancy markers, suggest that st-dECM bioink may be used as a more effective material in the field of new drug development and patient-specific tumor model development in the future.

3. Gastric Cancer Tissue Culture Using Different Bioink Concentrations

Tumor tissues in actual stomach cancer patients are harder than normal tissues. To simulate this fact, stomach cancer cells were cultured using controlled concentrations of the st-dECM bioink in order to harden the physical culture environment of stomach cancer cells. The culture method was as follows.

1) Stomach cancer cells were encapsulated in each of 1% (w/v) and 2% (w/v) st-dECM bioinks at a concentration of $5\times10^6$ cells/ml.

2) The cells were printed according to a designed pattern.

3) Thermal crosslinking was induced in an incubator at 37° C. for about 1 hour.

4) The stomach cancer cells were cultured using RPMI 1640 (supplemented with 10% FBS and 1% penicillin/streptomycin) medium.

It was confirmed through histological staining that, when 2% st-dECM bioink having a strength (376.6 Pa) which is about three times higher than that of 1% st-dECM bioink (129.8 Pa) was used, stomach cancer cells grew into larger aggregates, and that the expression levels of malignancy markers were also higher (FIG. 6). Thereby, it was verified that only the bioink of the present invention is capable of providing a physical environment, suggesting that the bioink may be used as a more effective material for preparing an in vitro stomach cancer model in the future.

The invention claimed is:

1. A method for decellularization of porcine stomach mucosal tissue comprising:

a chopping step of chopping porcine stomach mucosal tissue;

a first treatment step of immersing and maintaining the chopped porcine stomach mucosal tissue in a solution containing 0.5 to 2% (w/v) sodium dodecyl sulfate and 10 to 100 mM ethylenediaminetetraacetic acid for 12 to 48 hours;

a second treatment step of immersing and maintaining the stomach mucosal tissue, subjected to the first treatment step, in a solution containing 0.5 to 2% (w/v) polyethylene glycol p-(1,1,3,3-tetramethylbutyl)-phenyl ether and 10 to 100 mM ethylenediaminetetraacetic acid for 12 to 48 hours;

a washing step of washing the stomach mucosal tissue subjected to the second treatment step; and a third treatment step of immersing and maintaining the stomach mucosal tissue, subjected to the washing step, in a solution containing 0.05 to 0.2% (w/v) peracetic acid and 2 to 8% (v/v) ethanol for 1 to 4 hours;

wherein the porcine stomach mucosal tissue is tissue of a mucosa layer of a porcine stomach.

2. The method of claim 1, wherein the chopping step is a step of chopping the porcine stomach mucosal tissue to a thickness of 0.5 to 5 mm.

3. The method of claim 1, wherein the solution in the first treatment step is a solution containing 0.8 to 1.2% (w/v) sodium dodecyl sulfate and 20 to 30 mM ethylenediaminetetraacetic acid, the solution in the second treatment step is a solution containing 0.8 to 1.2% (w/v) polyethylene glycol p-(1,1,3,3-tetramethylbutyl)-phenyl ether and 20 to 30 mM ethylenediaminetetraacetic acid, and the solution in the third treatment step is a solution containing 0.08 to 0.12% (w/v) peracetic acid and 3 to 5% (v/v) ethanol.

4. The method of claim 3, wherein the first treatment step is a step of immersing and maintaining the chopped porcine stomach mucosal tissue in the solution containing sodium dodecyl sulfate and ethylenediaminetetraacetic acid for 20 to 30 hours with stirring, the second treatment step is a step of immersing and maintaining the stomach mucosal tissue, subjected to the first treatment step, in the solution containing polyethylene glycol p-(1,1,3,3-tetramethylbutyl)-phenyl ether and ethylenediaminetetraacetic acid for 20 to 30 hours with stirring, and the third treatment step is a step of immersing and maintaining the stomach mucosal tissue, subjected to the washing step, in the solution containing peracetic acid and ethanol for 1 to 3 hours with stirring.

5. The method of claim 1, wherein the washing step is a step of washing the stomach mucosal tissue, subjected to the second treatment step, with phosphate buffered saline.

6. A decellularization product composed of a porcine stomach mucosal tissue decellularized by the method of claim 1.

7. A composition for producing a stomach tissue or stomach cancer tissue culture scaffold comprising a pepsin digest of the decellularization product of claim 6.

8. The composition of claim 7, which is prepared by adding the decellularization product to an acetic acid-containing solution and adding pepsin thereto.

9. The composition of claim 8, which is prepared by adding, to a 0.25 to 1M acetic acid solution, the decellularization product at 0.5 to 4% (w/w) and pepsin at 0.025 to 0.8% (w/w).

10. A method for culturing stomach tissue or stomach cancer tissue comprising:

a step of producing a tissue culture scaffold containing stomach cells or stomach cancer cells by adding stomach cells or stomach cancer cells to the composition of claim 7, followed by shaping; and a culture step of culturing the tissue culture scaffold containing stomach cells or stomach cancer cells in a medium.

11. The method of claim 10, wherein the shaping is performed by 3D printing.

12. The method of claim 10, further comprising, before the culture step, a thermal crosslinking step of heat-treating the tissue culture scaffold containing stomach cells or stomach cancer cells at 35 to 40° C.

* * * * *